US00PP18737P3

(12) United States Plant Patent
Layt

(10) Patent No.: US PP18,737 P3
(45) Date of Patent: Apr. 22, 2008

(54) ***DIANELLA TASMANICA* PLANT NAMED 'TR20'**

(50) Latin Name: *Dianella tasmanica*
Varietal Denomination: TR20

(75) Inventor: Todd Anthony Layt, New South Wales (AU)

(73) Assignee: VersaScapes, L.L.C., Mt. Pleasant, SC (US)

( * ) Notice: Subject to any disclaimer, the term of this patent is extended or adjusted under 35 U.S.C. 154(b) by 0 days.

(21) Appl. No.: 11/238,477

(22) Filed: Sep. 29, 2005

(65) Prior Publication Data

US 2006/0075531 P1 Apr. 6, 2006

Related U.S. Application Data

(60) Provisional application No. 60/614,657, filed on Sep. 30, 2004.

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

2006/0075531 P1 4/2006 Layt ..... Plt./263

OTHER PUBLICATIONS

1(Royal Horticultural Society Dictionary of Gardening, 1992, vol. II D–K, McMillan Press, London; Stockton Press, New York, p. 49–50).

Layt; "Dianella tasmanica flax lily 'TR20,'" *Plant Varieties Journal* 16(4): 122 (Feb. 6, 2004).

Layt; "Dianella tasmanica flax lily 'TR20,'" *Plant Varieties Journal* 17(1): 603–605 (Apr. 28, 2004).

Australian Government, IP Australia, Plant Breeder's Rights; Database entry for Australian Plant Breeders Right Application No. 2003/290; Variety 'TR20' http://pbr.ipaustralia.optus.com.au/docs/2003290.doc.

*Primary Examiner*—Wendy C. Haas
*Assistant Examiner*—Georgia Helmer
(74) *Attorney, Agent, or Firm*—Myers Bigel Sibley & Sajovec, P.A.

(57) ABSTRACT

'TR20' is a distinctive variety of *Dianella tasmanica* with a clumping habit, which is characterized by the combination of a large flower cluster with blue flowers, green foliage with red basal shoots and red green lower leaf areas, which changes to a reddish-green foliage with red leaf margins in cooler seasons, and, in the Spring, TR20 leaf colour is yellow-green with some red leaf margins and red basal shoots and red-green lower leaf areas.

4 Drawing Sheets

Latin name of the genus and species: The Latin name of the novel variety disclosed herein is *Dianella tasmanica.*

Variety denomination: The inventive variety of *Dianella tasmanica* disclosed herein has been given the varietal denomination 'TR20'.

BACKGROUND OF THE INVENTION

The present invention relates to a new and distinct perennial Flax Lilly variety of *Dianella tasmanica,* which has been given the varietal denomination of 'TR20'. Its market class is that of an ornamental grass-like plant. 'TR20' is intended for use in landscaping and as a decorative grass-like plant.

An application for plant breeders' rights for variety 'TR20' has been filed with the Australian Plant Breeders' Rights Office, and was first gazetted in the Plant Varieties Journal in October 2003 under Application No. 2003/290.

Parentage. The *Dianella tasmanica* variety 'TR20' was first discovered in October 1996 in an Australian nursery in the state of New South Wales after an extensive breeding program. The parent, 'Southern Tablelands Ecotype', (unpatented) is characterized by a weak expression of basal leaf sheath reddening and reddening of the midrib and not the leaf margin in winter.

In 1995, *Dianella* species were grown together in an open bed covering approximately 250 square meters of area. They were grown in groups of species and ecotypes including

*Dianella tasmanica* collected from the Southern Tablelands area of Australia, and other regions. The other species present were *longifolia, revoluta* and *caerulea.* The plants were open pollinated with possible assisted pollination from general shaking of flower stems onto each other.

Seeds were collected and sown from the 'Southern Tablelands' plants in December 1995. Approximately 20,000 plants were grown. In August 1996, using the selection criteria of red basal leaf sheath colour and leaf redness, a single plant was identified as having a very red basal shoot and in wintertime a number of reddish leaves and red leaf margins. This plant was selected, potted into a 140 mm pot for further evaluation and named 'TR20'.

Asexual reproduction. 'TR20' was first asexually propagated by division in April 1997 in the state of New South Wales, Australia. 'TR20' was asexually reproduced again during November 1997 and April 1998 and confirmed to be stable in character. The distinctive characteristics of the inventive variety, 'TR20', have remained stable and true to type from generation to generation through successive cycles of asexual reproduction including vegetative division and micropropagation.

'TR20' has a clumping habit, green foliage with red basal shoots and red-green lower leaf areas, which changes to a reddish-green foliage in cooler seasons, with red leaf margins. In the Spring, 'TR20' leaf color is a yellow-green colour with some red leaf margins and red basal shoots and red-green lower leaf areas. 'TR20' has a large flower cluster, with blue flowers.

SUMMARY OF THE INVENTION

'TR20' is a distinctive variety of *Dianella tasmanica* with a clumping habit, which is characterized by the combination of a large flower cluster with blue flowers, green foliage with red basal shoots and red-green lower leaf areas, which changes to a reddish-green foliage with red leaf margins in cooler seasons, and in the Spring TR20 leaf colour is yellow-green with some red leaf margins and red basal shoots and red-green lower leaf areas.

BRIEF DESCRIPTION OF THE FIGURES

The photographs in the drawings were made using conventional techniques and show the colours as true as reasonably possible by conventional photography. Colours in the photographs may differ slightly from the colour values cited in the detailed botanical description, which accurately describe the colours of the new *Dianella tasmanica*.

BOTANICAL DESCRIPTION OF THE PLANT

The following is a detailed botanical description of a new and distinct variety of a *Dianella tasmanica* ornamental grass-like plant known as 'TR20'. The descriptions disclosed herein are based upon observations of the plant grown in 140 mm nursery pots and field plots in New South Wales, Australia. The plants were approximately 12-months-old at the time of observation. All colors cited herein refer to The Royal Horticultural Society Colour Chart (The Royal Horticultural Society, London, 2001 edition).

Those skilled in the art will appreciate that certain characteristics will vary with older or, conversely, younger plants. 'TR20' has not been observed under all possible environmental conditions. Where dimensions, sizes, colors and other characteristics are given, it is to be understood that such characteristics are approximations or averages set forth as accurately as practicable. The phenotype of the variety may differ with variations in the environment such as season, temperature, light intensity, day length, cultural conditions and the like.

Figure 1:
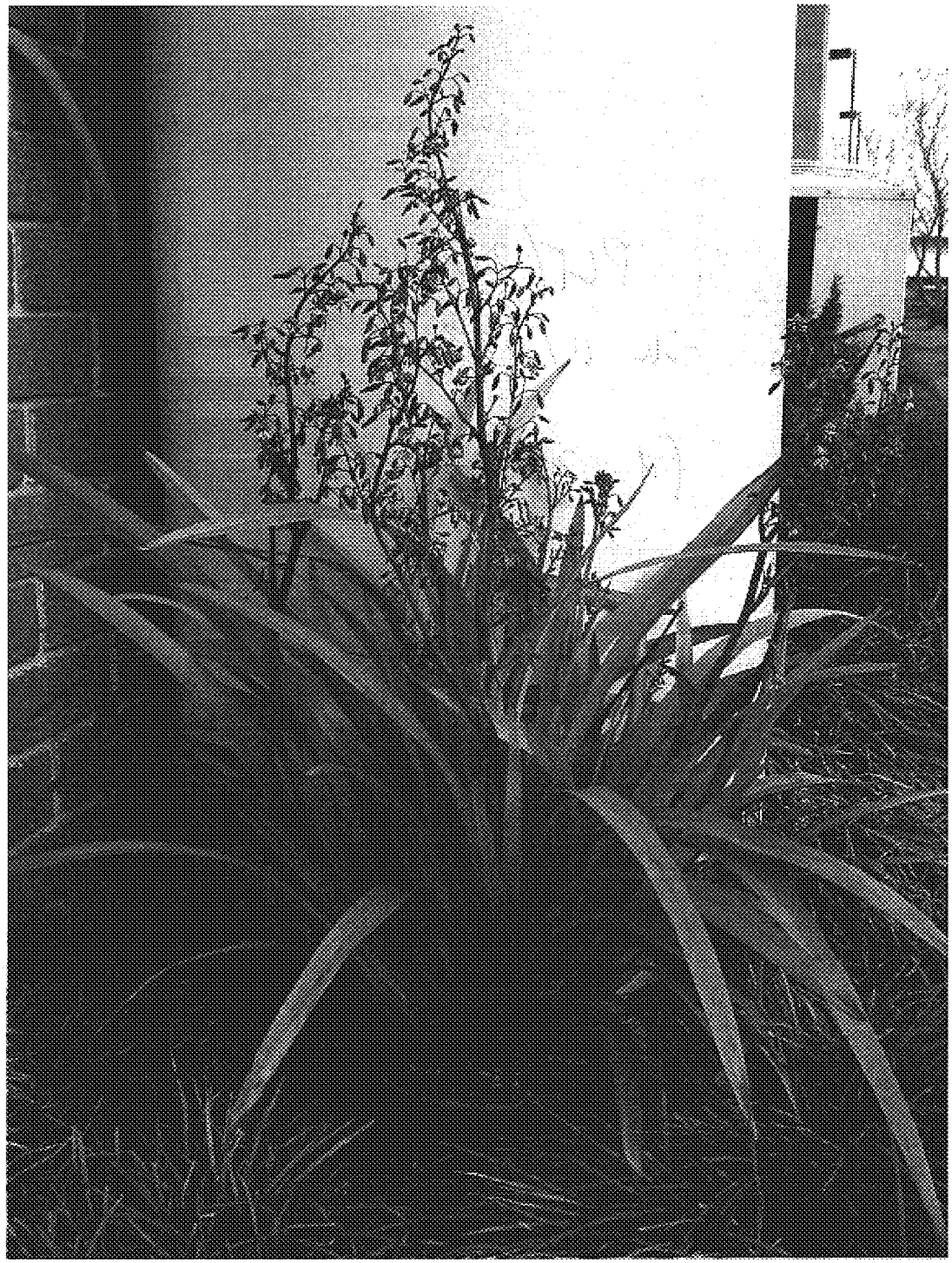
FIG. 1 shows a 'TR20' plant in Spring with red basal shoots, yellow-green leaf colour, lower leaf red-green colour, red flower stem colour, and large flower cluster.
Figure 2:
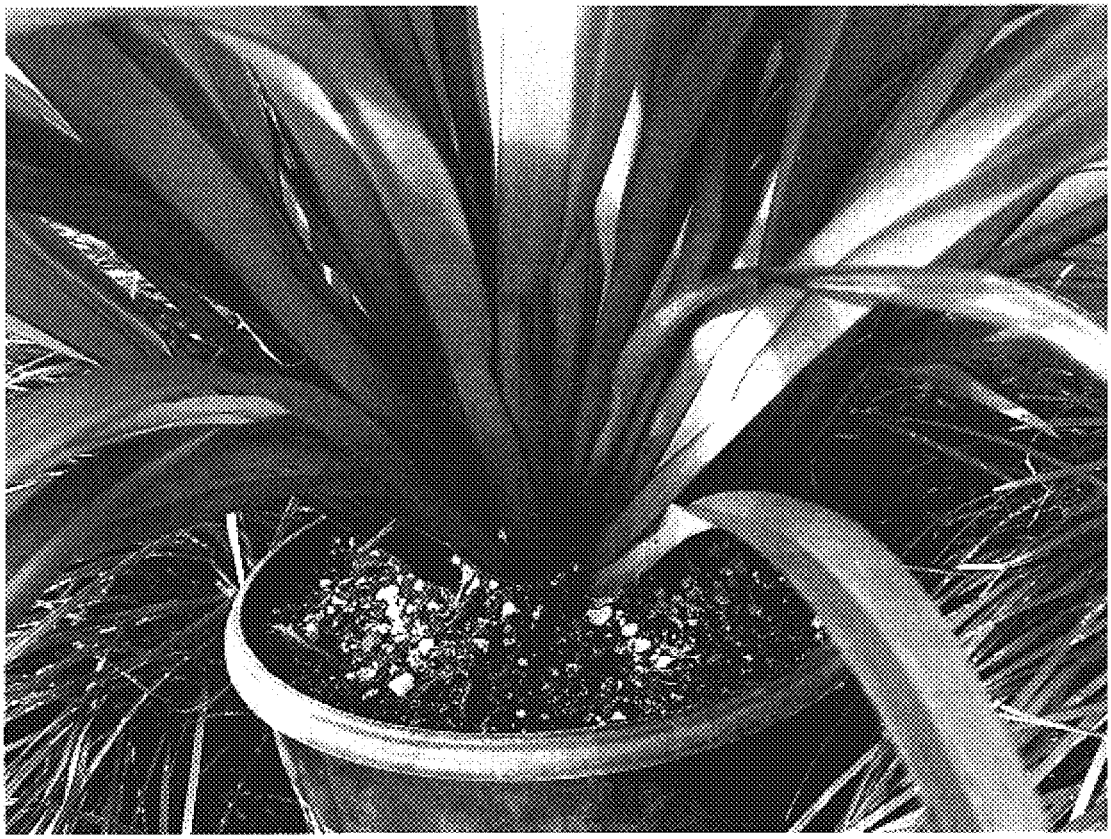
FIG. 2 shows a close-up of the red lower leaf and red basal shoot colour of 'TR20' plant in Spring.
Figure 3:
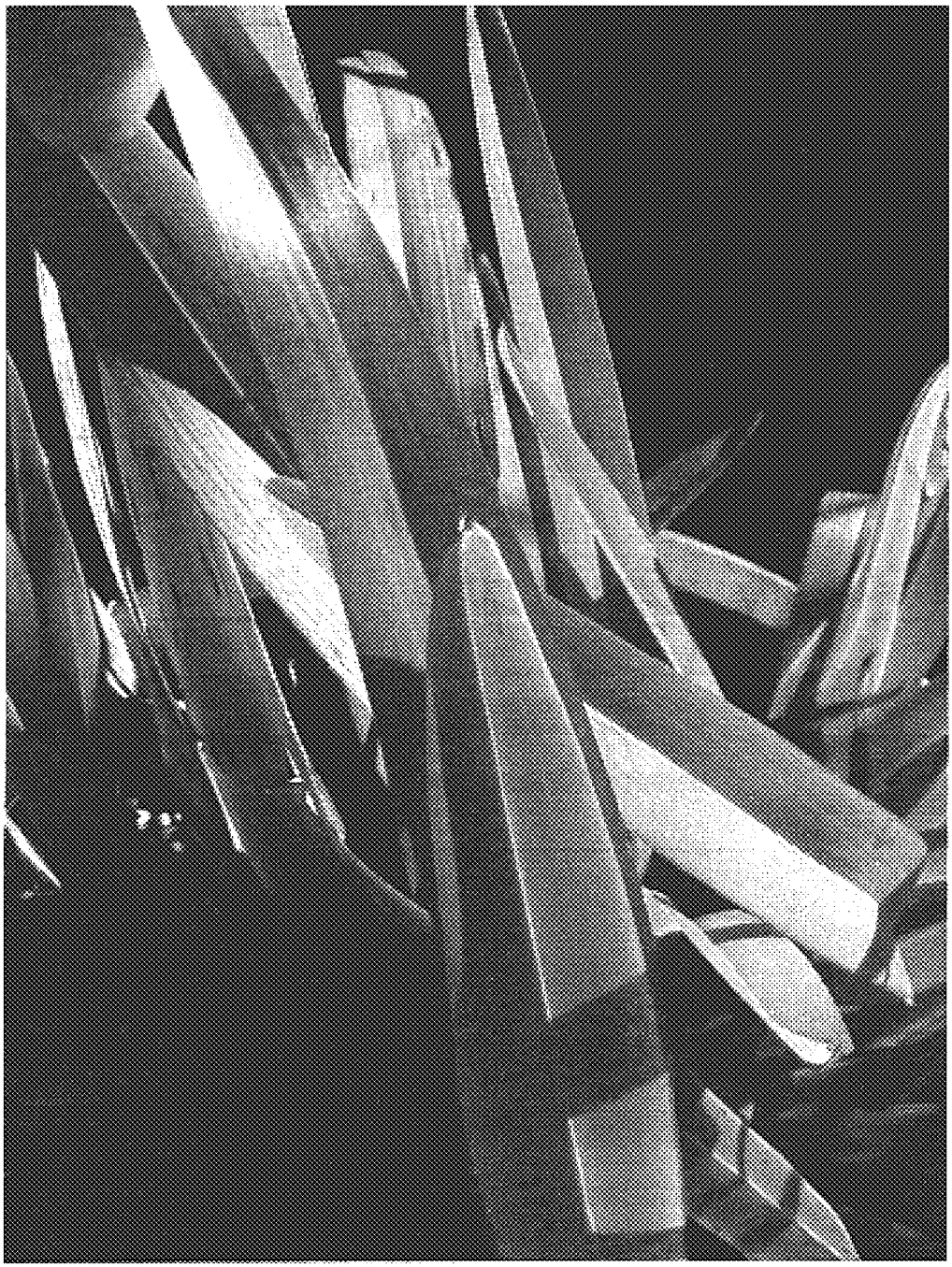
FIG. 3 shows the red colour of some leaves of 'TR20' in Winter.
Figure 4:
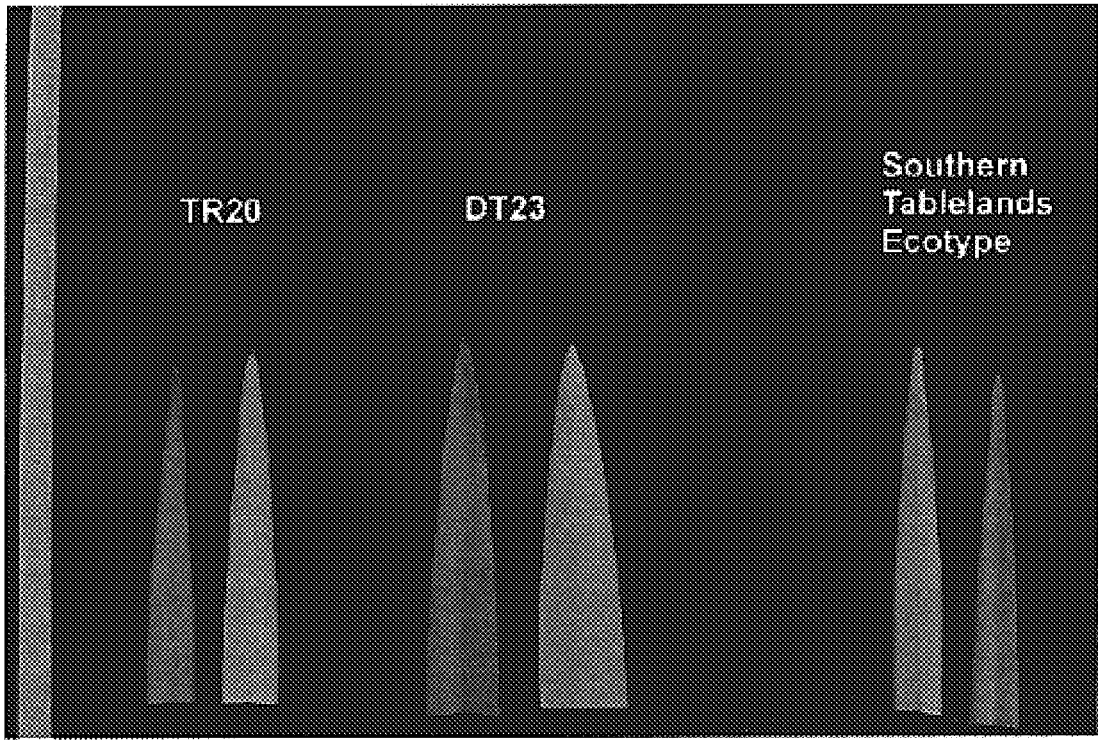
FIG. 4 shows variations in leaf width among different *Dianella tasmanica* varieties including 'TR20', 'Southern Tablelands Ecotype' and 'DT23' (U.S. Provisional Application Ser. No. 60/652,056, filed Feb. 11, 2005).

'TR20' is a perennial *Dianella tasmanica* plant which was produced through an innovative breeding program. After its selection, 'TR20' was asexually propagated by division and micropropagation. 'TR20' has a clumping form, green foliage with red basal shoots and red-green lower leaf areas, which changes to a reddish-green foliage in cooler seasons, with red leaf margins, and a yellow-green leaf colour in the Spring with some red leaf margins and red basal shoots and lower leaf areas. 'TR20' also has a large flower cluster, with blue flowers and yellow anthers. A botanical description of 'TR20' and a comparison with other varieties of *Dianella tasmanica* are provided below. Representative *Dianella tasmanica* 'TR20' plants are illustrated in FIG. 1 and FIG. 2.

Technical Description of the Variety.

Growth Habit. 'TR20' forms a clumping tussock with an erect to semi-erect growth habit. 'TR20' has a medium height (mean 28 cm) and medium density of shoots.

Stem. Length of internodes is short.

Foliage. Leaf attitude is erect to semi-erect, arching medium, width medium (mean 20 mm); upper side colour with waxiness removed is yellow-green (RHS 146A), lower side colour with waxiness removed is yellow-green (RHS 146B), upper side glaucosity is absent to very weak, shape is ligulate, apex acute, cross section concave, spines on the margin are present with medium prominence, margin colour in winter is red, spines on lower side midrib are present with medium prominence.

Basal shoots. The basal shoots are red (approximately RHS 183A), with red-green lower leaves (approximately RHS 183A) mixing in with the yellow green (RHS 146A) of the leaf color.

Basal sheath. Anthocyanin colour (Summer) red-brown (approximately RHS 187B-C to 185A and 185B at the base), intensity of anthocyanin colour medium-strong.

Inflorescence. The inflorescence (flower spike) is a panicle with a length in the range of 55-70 cm. The inflorescence is positioned above the level of the foliage. The flower spike is soft to the touch. Peduncle color is yellow green (approximately RHS 146B-C). Flowering season is late spring-summer.

Flowers: The flower buds are 8-10 mm long and 3-4 mm wide. Bud color changes from yellow green (RHS 147B) to violet blue (approximately RHS 89A) prior to opening. Mature flowers have 6 petals with ovate shape. Petal color is violet-blue (approximately RHS 94B) in the centre and violet-blue (approximately RHS 97B) at the margin. Anther filament color is yellow (approximately RHS 12A). Flower diameter range is 10-13 mm. Petal attitude is strongly reflexed.

Fruit: A succulent berry, length to 20 mm, shape is globose to oblong, color of unripe berry is yellow green (RHS 146A) and color of ripe berry is approximately violet blue (RHS 89A), surface texture is smooth and glossy. Seed color is black.

Environmental Tolerances. 'TR20' has shown potential for shade tolerance. The winter hardiness of 'TR20' is at least to −12 degrees Celsius. 'TR20' has good color retention, with changing foliage colour in winter. Colour changes of 'TR20' have been observed at temperatures of 4 degrees Celsius. 'TR20' with normal drought tolerance as compared to the common form of this plant.

Disease Resistance and Susceptibility. 'TR20' has good tolerance to pests and diseases. Tolerance to diseases can refer to root rot which is caused by the disease causing organism *Phytophthora*. Tolerance to pests can refer to no damage from snails, slugs, mites, aphids, whitefly, beetles, caterpillars and moths.

These features and other characteristics of the plant are apparent from the figures provided herein.

'TR20' Compared to Other Varieties of *Dianella tasmanica*.

Grouping characteristics used to identify the most similar varieties of common knowledge included medium-tall plant height and an erect to semi-erect growth habit. Based on this, the parent ('Southern Tablelands Ecotype') was selected as the most similar suitable comparator. *D. tasmanica* 'DT23' was also included in the trial. No other similar varieties were identified.

The comparative trial of *Dianella tasmanica* 'TR20' with other varieties of *D. tasmanica* including 'Southern Tablelands Ecotype', and 'DT23', was carried out in Summer 2002 through Autumn 2003 in Clarendon, New South Wales, Australia. The trial was conducted in open beds. The plants for this trail were propagated from divisions and planted into 130 mm pots filled with soilless potting mix. Nutrition was maintained with slow release fertilizers and pest and disease treatments were applied as required. The plants did not flower during the trial. Trial design included fifteen pots of each variety arranged in a completely randomised design. Measurements were taken from ten plants at random with one sample taken per plant.

In comparing 'TR20' to the parent, 'Southern Tablelands Ecotype', and other ecotypes including the 'Tasmanian Ecotype' (unpatented), 'TR20' has a more red basal shoot and more red lower leaf. The leaf of 'TR20' changes to a reddish-green foliage in cooler seasons, with red leaf margins, and in the Spring the leaf colour is yellow-green with some red leaf margins and red basal shoots and red-green lower leaf areas. This amount of seasonal colour change is unusual for a *Dianella tasmanica;* the 'Southern Tablelands Ecotype' and other ecotypes including the 'Tasmanian Ecotype' do not show the seasonal colour changes as exhibited in 'TR20'. 'TR20' has more red flower stems compared to the 'Southern Tablelands Ecotype', and other ecotypes including the 'Tasmanian Ecotype'. In comparing 'TR20' to 'DT23', 'DT23' has a much broader leaf width than 'TR20' and much less basal sheath redness. The basal sheath of 'DT23' is green with a red-brown margin whereas 'TR20' is all red-brown without the green. Further comparisons are presented in Table I.

TABLE I

Comparison of three varieties of *Dianella tasmanica.*

| | 'TR20' | 'DT23' | Southern Tablelands Ecotype |
|---|---|---|---|
| PLANT: GROWTH HABIT | erect to semi-erect | erect to semi-erect | erect to semi-erect |
| PLANT HEIGHT (cm) LSD (P ≦ 0.01) = 4.33 | | | |
| Mean | 28[b] | 34.2[a] | 31.5[ab] |
| Std deviation | 1.9 | 4.5 | 5.7 |

TABLE I-continued

Comparison of three varieties of *Dianella tasmanica.*

| | 'TR20' | 'DT23' | Southern Tablelands Ecotype |
|---|---|---|---|
| PLANT: DENSITY OF SHOOTS | medium | medium | medium |
| STEM: INTERNODE LENGTH | short | short | short |
| LEAF: WIDTH (mm) LSD (P ≦ 0.01) = 1.81 | | | |
| Mean | 20.0[b] | 29.1[a] | 21.3[b] |
| Std deviation | 1.7 | 1.6 | 2 |
| LEAF: FOLIAGE COLOUR - overall appearance of leaf | yellow-green | green | yellow-green |
| LEAF: COLOUR - waxiness removed | | | |
| Upper side | 146A | 147A | 147A |
| Lower side | 146B | 147B | 147B |
| LEAF: GLAUCOSITY | absent-very weak | weak | absent-very weak |
| LEAF: PRESENCE OF SPINES ON MARGIN | present | present | present |
| LEAF: PROMINENCE OF SPINES ON MARGIN | medium | medium | strong |
| LEAF: PRESENCE OF SPINES ON LOWER SIDE MIDRIB | present | present | present |
| LEAF: PROMINENCE OF SPINES ON LOWER SIDE MIDRIB | medium | strong | medium |
| BASAL SHEATH: COLOUR (summer) | red-brown | green with margin red-brown | red-brown |
| BASAL SHEATH: INTENSITY OF ANTHOCYANIN COLOUR | medium-strong | weak | medium |

Mean values followed by the same letter are not significantly different at P ≦ 0.01 according to an S-N-K test.

That which is claimed is:

1. A new and distinct variety of *Dianella tasmanica* plant named 'TR20', substantially as described and illustrated herein.

* * * * *